United States Patent
Price et al.

(10) Patent No.: US 8,128,799 B2
(45) Date of Patent: Mar. 6, 2012

(54) WELDED ELECTROPHORESIS CASSETTE WITHOUT LEAKAGE-PRONE WELD LINE

(75) Inventors: Glenn Price, Martinez, CA (US); Cory Panattoni, Winters, CA (US); Craig Rowell, Albany, CA (US); Shane Petersen, Fairfield, CA (US); Evelio Perez, Richmond, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 291 days.

(21) Appl. No.: 12/437,698

(22) Filed: May 8, 2009

(65) Prior Publication Data

US 2009/0308751 A1 Dec. 17, 2009

Related U.S. Application Data

(60) Provisional application No. 61/052,501, filed on May 12, 2008.

(51) Int. Cl.
*C02F 1/48* (2006.01)
*C02F 1/40* (2006.01)
*C25B 9/00* (2006.01)
*C25B 11/00* (2006.01)
*C25B 13/00* (2006.01)
*G01N 27/00* (2006.01)

(52) U.S. Cl. .................................. 204/616
(58) Field of Classification Search .............. 204/616, 204/615, 618, 619; 425/291, 290
See application file for complete search history.

(56) References Cited

U.S. PATENT DOCUMENTS

| | | | |
|---|---|---|---|
| 4,889,480 A | 12/1989 | Nakamura et al. | |
| 4,954,236 A | 9/1990 | Kushner et al. | |
| 5,411,657 A * | 5/1995 | Leka | 204/618 |
| 5,827,418 A * | 10/1998 | Haven et al. | 204/618 |
| 6,093,301 A | 7/2000 | Van Atta | |
| 6,099,785 A | 8/2000 | Schweigert et al. | |
| 6,287,106 B1 | 9/2001 | Learn et al. | |
| 7,135,101 B2 | 11/2006 | Atchison et al. | |
| 2001/0037940 A1 | 11/2001 | Shih et al. | |
| 2006/0273489 A1 | 12/2006 | Shakal | |
| 2007/0242978 A1 | 10/2007 | Wazana et al. | |

OTHER PUBLICATIONS

Waterson, Joanne; "Failure Analysis of a Four Gang Trailing Socket"; 2008, http://www.the-tpa.org.uk/consultants_corner/jwaterson_Top_tip.htm, 3 pages.

* cited by examiner

*Primary Examiner* — Jeffrey T Barton
*Assistant Examiner* — Louis Rufo
(74) *Attorney, Agent, or Firm* — Kilpatrick Townsend and Stockton LLP.; M. Henry Heines

(57) ABSTRACT

A slab gel cassette is formed from generally flat plates welded together along their borders with a gel space between the plates that is open at the top and bottom edges of the plates to expose the opposing ends of a gel in the gel space to buffer solutions in which electrodes are immersed. The plates are shaped such that the weld line does not intersect with the bottom opening of the gel space. Sealing of the bottom of the gel space, which is necessary for gel casting, is achieved by placing a sealing strip over the bottom opening with no danger of leakage of the gel solution along a weld line.

5 Claims, 4 Drawing Sheets

WELDED ELECTROPHORESIS CASSETTE WITHOUT LEAKAGE-PRONE WELD LINE

CROSS-REFERENCE TO RELATED APPLICATION

This application claims the benefit of U.S. Provisional Patent Application No. 61/052,501, filed May 12, 2008, the contents of which are incorporated herein by reference.

BACKGROUND OF THE INVENTION

1. Field of the Invention

This invention resides in the field of biochemical laboratory equipment, and specifically equipment for slab gel electrophoresis.

2. Description of the Prior Art

Electrophoresis in slab-shaped gels is a common analytical technique in biotechnical laboratories in view of the many beneficial features that slab gels offer to the analytical chemist or biochemist. A slab gel can be divided, for example, into several lanes and a separate analysis can be performed in each lane while all are performed under the same conditions. Also, slab gels are easily removed from their enclosures for staining to make the solute bands visible. Further, the flat, two-dimensional configuration of a slab gel allows the gel to be easily scanned for identification and quantification of the contents of each band by automated instrumentation.

Slab gels are commonly held in cassettes that essentially consist of a pair parallel plates separated by a gap that defines the thickness of the gel. The gel is cast in the cassette by filling the gap with a solution of the gel-forming monomer or prepolymer and allowing the solution to polymerize. Once the gel is cast, samples are loaded along the top edge of the gel and electrophoresis is performed with the top and bottom edges of the gel in contact with electrodes through buffer solutions. Examples of cassettes of this type are those described in Leka, U.S. Pat. No. 5,411,657, May 2, 1995, and Van Atta, U.S. Pat. No. 6,093,301, Jul. 25, 2000.

Casting the gel in the manner described above requires temporary sealing of the bottom edge of the gel space in such a manner that removal of the seal leaves the gel with a cleanly defined bottom edge. A commonly used seal is a strip of flexible adhesive-backed tape. While the tape can be removed without tearing the gel, a difficulty with this method is that the two plates are typically welded together along their side edges leaving a weld line where the plates meet, and the weld line, even when covered by the tape, is a common site for leakage. To avoid this, cassettes have been designed with a closed bottom and a slot in one of the plates near and parallel to the bottom. The resulting gel has a "foot" along its lower edge that protrudes laterally through the slot. The foot deviates from the planarity of the remainder of the gel, however, which lowers clarity and accuracy during detection of the bands in the gel.

SUMMARY OF THE INVENTION

The present invention resides in a cassette that is formed by two flat plates and that exposes the lower edge of the gel without either forming a foot at the lower edge or leaving a weld line at the lower edge. Although the cassette is formed from two plates welded together, the lower edge of one of the plates is thick enough to span the full width of the gel space, and the opening is a slot in the thickened edge that is aligned with the gel space. The slot-shaped opening is thus surrounded by an unbroken surface that is readily sealed with tape. As alternatives to tape, the opening can be sealed with a soft rubber plug or a sealing pad compressed against the opening by an externally applied force. In each case, the unbroken surface around the opening will enhance the seal.

More particularly, the two plates forming the cassette are rectangular plates, with two parallel lateral edges and two parallel end edges, typically welded together along both lateral edges and one of the two end edges. The lateral edges along one or both of the plates are raised, and the welding is along the raised edges. Welding is also used for joining the plates along the thickened lower edge but at a site removed from the peripheral surface surrounding the slot-shaped opening. This peripheral surface is thus smooth with no surface discontinuities, and thus capable of being sealed without leakage along a weld line. In addition, the thickened lower edge is preferably breakable at controlled sites to allow the plates to be separated so that the gel can be removed after electrophoresis has been performed, without the need for opening the welds. The breakage sites can, for example, be established by scoring in the plate material along the edge, such as at the inner surface of the slot-shaped opening, or by notices in the inner surface. The peripheral surface will thus be narrower at these sites to focus the breakage, without compromising the continuity of the peripheral surface itself prior to the breakage.

These and other objects, features, and advantages of the invention and its preferred embodiments will be apparent from the Figures hereto and the description that follows.

DESCRIPTION OF THE PREFERRED EMBODIMENTS

Figure 1:
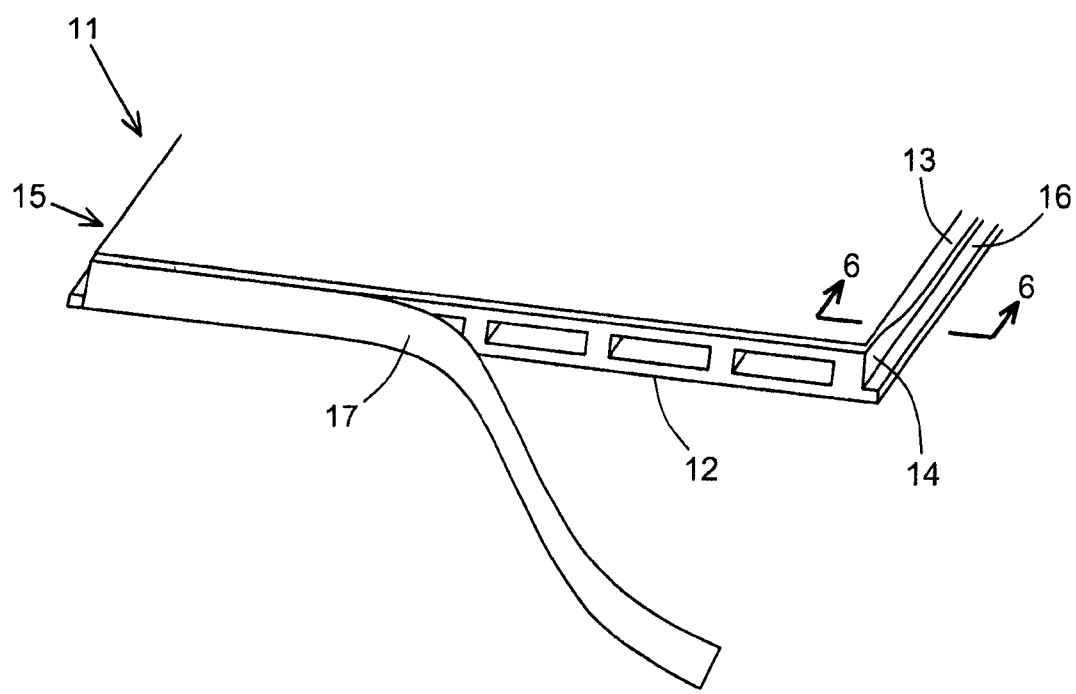
FIG. 1 is a perspective view of one end of a slab gel electrophoresis cassette in accordance with the present invention.

In FIG. 1, one end of a cassette 11 illustrating the features of the present invention is shown in perspective view lying on its side in a horizontal position. The end shown is the bottom end 12 which will face downward when the cassette is held in a vertical position for casting of a gel. The two plates, including the front plate 13 and the back plate 14, will likewise be vertical, as will the lateral edges 15, 16. During the casting of the gel, the bottom end 12 of the cassette is sealed by a sealing strip 17, shown partially removed in the Figure. When the cassette and the gel inside it are ready for electrophoresis, the sealing strip 17 will be removed entirely.

Figure 2:
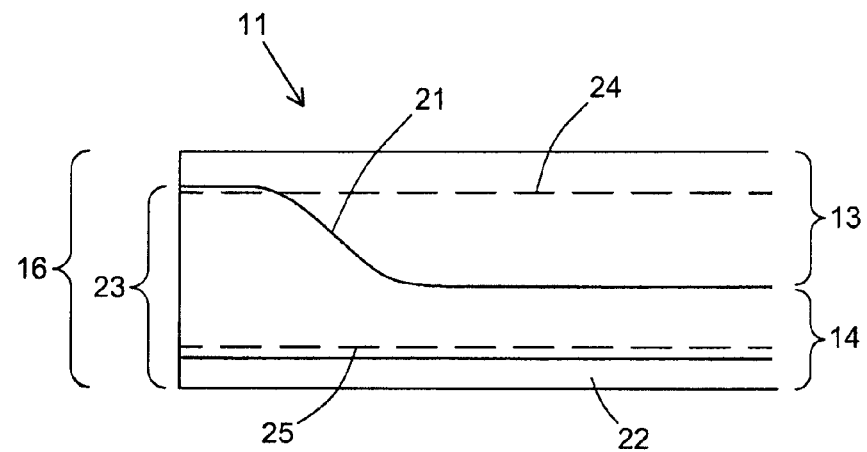
FIG. 2 is a side view of the cassette of FIG. 1.

A section of one of the lateral edges 16 of the cassette is shown in FIG. 2. The front plate 13 and the back plate 14 are welded together along their contacting surfaces 21 which are the tops of the raised lateral edges, and more visible in the succeeding Figures. The back plate 14 has a lateral flange 22 that secures the cassette in an electrophoresis cell, and a thickened lower edge 23. The front plate 13 is correspondingly thinner at its lower edge to accommodate the thickened lower edge 23 of the back plate 14. The lateral edges of both plates are raised relative to the plates themselves, in this case to heights that vary along the lengths of the edges, with complementary contours to provide full contact when joined. The flat opposing surfaces of each of the plates adjacent to the lateral edges, are shown in dashed lines 24, 25, and the space between them is the gel space, which is enclosed on both sides by the raised lateral edges.

Figure 3A:
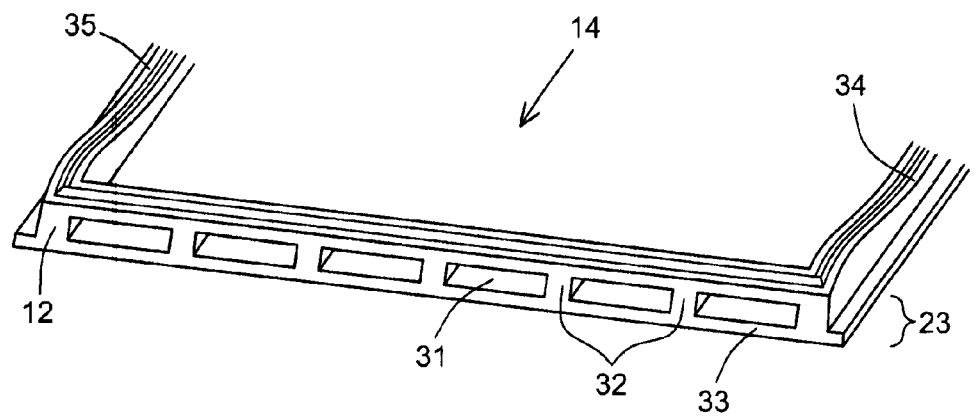
FIG. 3A a perspective view of the back plate of the cassette of FIG. 1, from the same angle as FIG. 1.
Figure 3B:
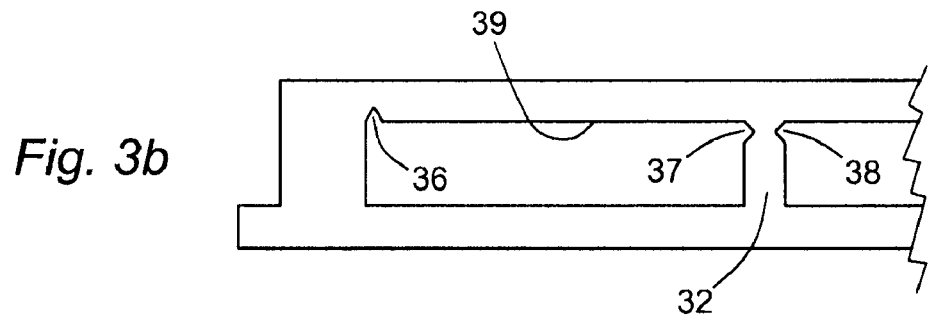
FIG. 3B is a partial end view of the back plate of the preceding Figures.
Figure 3C:
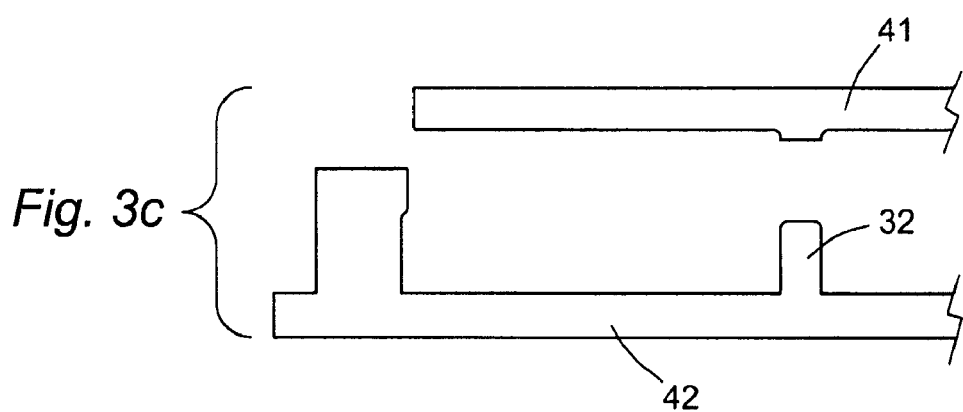
FIG. 3C is the same view as FIG. 3B except with the back plate broken to release the gel from the slot-shaped opening.

FIG. 3A is a view of the bottom edge 12 of the back plate 14, prior to being welded to the front plate and to being sealed with the sealing tape. The bottom edge 12 of the back plate 14 has an elongated slot-shaped opening 31 that is interrupted by one or more piers 32 or strengthening ribs that add structural stability to the plate and the opening. The opening is the lower terminus of the gel space and exposes the lower end of the gel during electrophoresis. The peripheral surface 33 surrounding the interrupted opening is smooth, flat, and free of discontinuities, and contains no weld lines. Welding is instead performed along the raised lateral edges 34, 35 and the bottom, thickened edge 23 of the plate along three sides of the gel space. The border has a contoured profile to accommodate the thickened edge 23 and, as shown in FIG. 2, the contour is complementary to that of the raised border of the front plate. FIG. 3B is an enlarged view of one end of the thickened edge 23 showing break points 36, 37, 38 where the slot-shaped opening 31 can be broken open to facilitate the removal of the gel slab after an electrophoresis procedure. The break points in this case are small notches or score lines on the inner surface 39 of the slot-shaped opening. FIG. 3C shows the two parts 41, 42 resulting from the break.

Figure 4:
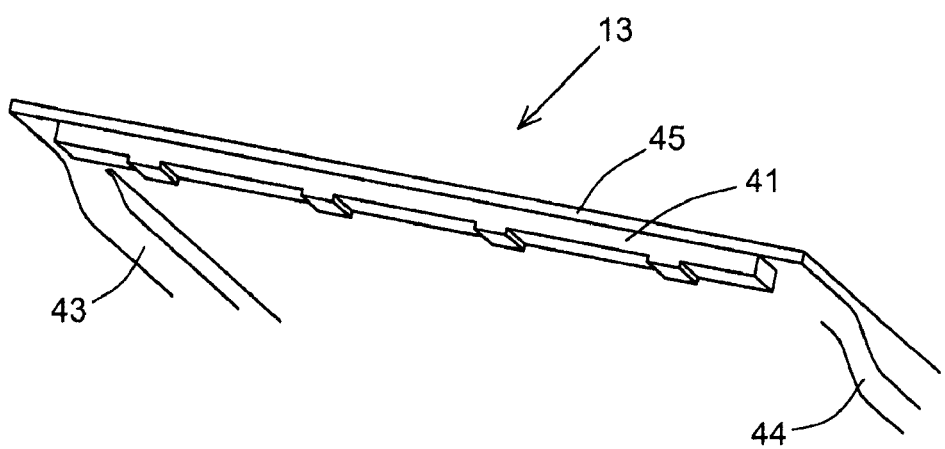
FIG. 4 is a perspective view of the front plate of the cassette of FIG. 1, from the underside of the plate.

FIG. 4 shows the front plate 13 in a view of the underside of the plate, showing the raised lateral edges 43, 44 of the plate which, together with the surface adjacent to the lower edge 45 of the front plate, are welded to the edges of the back plate. The gel space is bordered by the raised lateral edges 34, 35 (FIG. 3a) of the back plate, the raised lateral edges 43, 44 of the front plate, and the thickened end edge 23 of the back plate. The front plate 13 is shown as it appears after the electrophoresis has occurred and after the front and back plates have been broken apart to release the gel. As a result of the break, the upper part 41 of the bottom edge of the back plate has become separated from the rest of the back plate and remains welded to the front plate 13.

Figure 5:
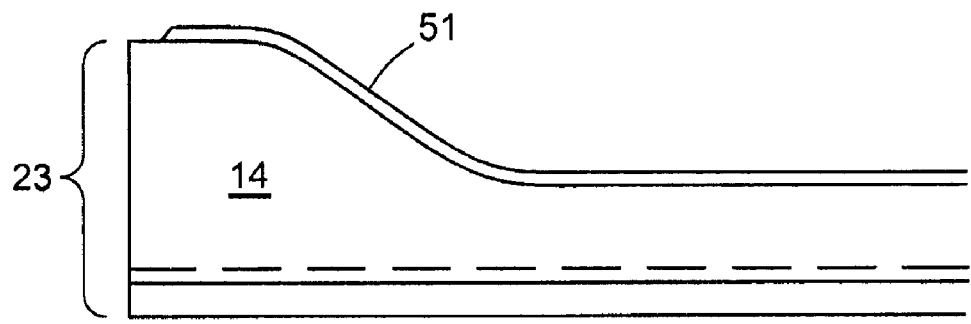
FIG. 5 is a side view of the back plate of the cassette of FIG. 1.
Figure 6:
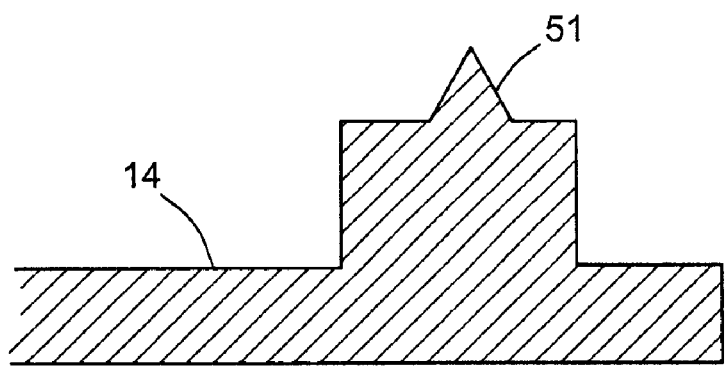
FIG. 6 is a cross section of the raised lateral edge of the black plate, taken along line 6-6 of FIG. 1.

While the plates can be formed and joined together by any conventional means, the plates are preferably formed separately by injection molding and welded together by ultrasonic welding. The thickened edge 23 of the back plate can be formed by an undercut section of the mold, appropriately equipped with a slide to release that portion of the plate from the mold. Mold designs and slides that are capable of containing undercut portions and releasing the molded part from the undercut are well known among those skilled in the art. Ultrasonic welding is likewise well known, and an energy director such as is likewise well known in the art can be included to assure a secure and continuous weld. The energy director is a feature on one of the parts to be welded that serves as the initial contact point with the other part, and is shaped to cause the ultrasonic vibrations to be focused on the point and thereby melt the part at that point such that the molten material flows across the weld face prior to being cooled. In the embodiment shown in the drawings, the energy director is a ridge with the profile of an inverted V running along the border of the back plate, and the weld faces are the borders of the two plates adjacent to the gel space. The ridge 51 is shown in a side view in FIG. 5 and in a cross section view in FIG. 6.

In the claims appended hereto, the terms "a," "an," and "one" are intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A cassette for retaining a slab gel to be used as an electrophoretic separation medium, said cassette comprising first and second rectangular plates, each with opposing parallel lateral edges and opposing parallel end edges, said lateral edges on one of said plates being raised and welded to said lateral edges on the other of said plates to define a slab-shaped gel space between said plates, and one of said end edges being sufficiently thick to span said gel space and having a slot-shaped opening aligned with said gel space, said slot-shaped opening surrounded by a smooth peripheral surface with no surface discontinuities and having an inner surface that is scored at selected sites to facilitate breakage of said thickened end edge across said peripheral surface.

2. The cassette of claim 1 wherein said slot-shaped opening is interrupted by a rib.

3. The cassette of claim 1 wherein said slot-shaped opening is interrupted by a plurality of ribs.

4. The cassette of claim 1 wherein said plates are formed by injection molding.

5. The cassette of claim 1 wherein said plates are formed by injection molding and welded together along said lateral edges and said thickened end edge by ultrasonic welding.

* * * * *